United States Patent [19]

Hastings

[11] Patent Number: 5,330,530

[45] Date of Patent: Jul. 19, 1994

[54] FIBER PROSTHESIS AND METHOD OF IMPLANTATION IN LIVING TISSUE

[76] Inventor: John L. Hastings, 385 River Valley Rd., Atlanta, Ga. 30328

[21] Appl. No.: 982,998

[22] Filed: Nov. 30, 1992

[51] Int. Cl.$^5$ ............................................. A61F 2/10
[52] U.S. Cl. ........................................ 623/15; 623/66
[58] Field of Search ............................... 623/15, 11, 66

[56] References Cited

U.S. PATENT DOCUMENTS 3,831,202  8/1974  Hulsen ................................. 623/15
4,054,954  10/1977  Nakayama et al. ................. 623/15

FOREIGN PATENT DOCUMENTS 2656207  6/1978  Fed. Rep. of Germany ........ 623/15
3812779  10/1989  Fed. Rep. of Germany ........ 623/15

Primary Examiner—David Isabella
Assistant Examiner—Debra S. Brittingham

[57] ABSTRACT

A method of treating baldness by securing hair fibers to a person's scalp is disclosed. A base filament is implanted into an incision in a subcutaneous layer of a scalp. A plurality of monofilament anchors extend perpendicularly from the base filament. With a length sufficient to span the dermis and epidermis, the anchor filaments terminate in an eyelet with the tip of the eyelet exposed at the surface of the scalp. Hair fibers are attached to the anchor filaments by threading hair filaments through the eyelets at the scalp surface.

1 Claim, 10 Drawing Sheets

FIBER PROSTHESIS AND METHOD OF IMPLANTATION IN LIVING TISSUE

BACKGROUND OF THE INVENTION

This invention is a treatment for baldness. While numerous treatments for baldness have been attempted, each has associated problems that this method will resolve.

Initial attempts to treat baldness involved hairpieces. A hairpiece consists of a base mesh to which individual hairs are attached. A sufficient quantity of hair must be attached to the mesh to completely conceal the mesh itself. This frequently results in an unnatural fullness in the hairpiece. This is especially true for people middle-aged and older who would normally have naturally thinning hair. The primary problem with this treatment involves the attachment of the hairpiece to the scalp. When a large area of the scalp must be covered, the weight of the hairpiece exacerbates the attachment problem. The attachment process usually involves adhesives, such as double sided tape, which tend to loosen when mixed with oils and perspiration normally present on the scalp. In addition, most of these adhesives are arduous to remove during cleaning. To insure proper bonding with new adhesive, old adhesive must be thoroughly removed prior to each cleaning of the hairpiece. Depending upon the degree and type of activity, this cleaning process may be required several times each week.

Several attempts to remedy the attachment problem involved tying the hairpiece to growing hair on the head. Unfortunately, as the growing hair grows, the replacement hair becomes loose and must be periodically tightened. Because hair grows at an approximate rate of one-half inch per month, the tightening is normally required at frequent intervals.

Other attachment procedures utilized sutures implanted in the scalp with the replacement hair attached to the portion of the sutures exposed above the scalp. This relatively permanent attachment made cleaning difficult, especially in the area of the sutures, resulting in chronic infection. One attempt to resolve this problem utilized wefts, a single filament with hair attached, tied to rows of sutures, giving greater access to clean the suture area. However, high stress due to the relatively large number of hairs per suture caused many of the sutures to cut through the scalp, causing infection and requiring frequent replacement.

Other attempts to treat baldness involved the implantation of fibers directly into the scalp. Every attempt involved insertion of the hair into the scalp by a puncture performed with a needle-like tool. Initial attempts used single strands of hair. Subsequent attempts used multiple strands or single strands that were weaved in and out of the scalp and subsequently cut to create the appearance of single hairs emerging from the scalp. In each of these methods, the scalp relied upon to retain the hair. In most cases, normal grooming caused the hair to pull from the hole in the scalp. Numerous methods attempted to solved this problem through the use of various knots and loops, however, elasticity of the scalp resulted in failure of each of these attempts.

A surgical method that has met with limited success involves the use of transplanted hair. Small plugs of scalp containing hair follicles are removed from the back of the head and transplanted to the balding areas of the head. This procedure does not add any hair to the scalp, but simply relocates the existing hair. Therefore, it is limited to those with relatively minor hair loss. Large areas of the scalp cannot be covered sufficiently with this method, especially if the donor site is limited.

SUMMARY OF THE INVENTION

The invention comprises a plurality of monofilament anchors to a base filament. The base filament is inserted into an incision made in the scalp. The incision is closed through the use of sutures and/or tissue adhesives or any other means, leaving the base filament embedded beneath the scalp. The anchors rise from the base filament to the surface of the scalp, where hair fibers can be attached to an eyelet at the termination of the anchor. The hair fibers may be attached as individual fibers or as clusters of fibers, depending upon the effect desired. Alternately, the base filament may be threaded through a puncture in the scalp with the anchors sewn through the scalp. The base filament and anchors are made from materials which are medically inert to the scalp. The base filament and anchors may be made from an inert metal, such as gold, or synthetic material similar to that of permanent sutures. Sufficient space is maintained between the anchors so the scalp can heal around them. Once healed, the scalp will retain the base filament and the anchors will remain in place. It is intended that the base filaments will be cut to various lengths, depending upon the area of the scalp to be covered. Rows of these filaments can be implanted within sufficient proximity to each other such that the hair density will resemble normal growing hair.

DETAILED DESCRIPTION OF THE DRAWINGS

Figure 1:
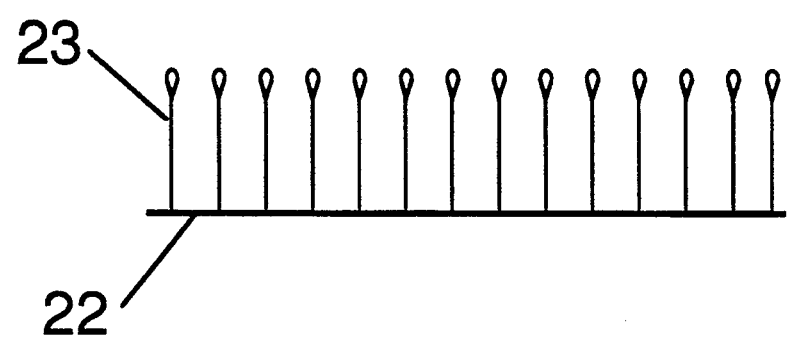
FIG. 1. is a drawing of the base filament with anchors attached in preparation for implanting.

The embodiment of the invention shown in FIG. 1 illustrates monofilament anchors 23 attached to a base filament 22 prior to implantation in the scalp. Specifically, a plurality of anchors are attached to or made integral with a base filament 22. Made from a tissue inert material, the implant can be manufactured to any length suitable for implantation. The anchor filaments should have sufficient separation to allow the scalp to heal around the filaments following implantation. This healing is important from the standpoint of securing the implants as well as protecting the scalp from bacterial invasion.

Figure 2:
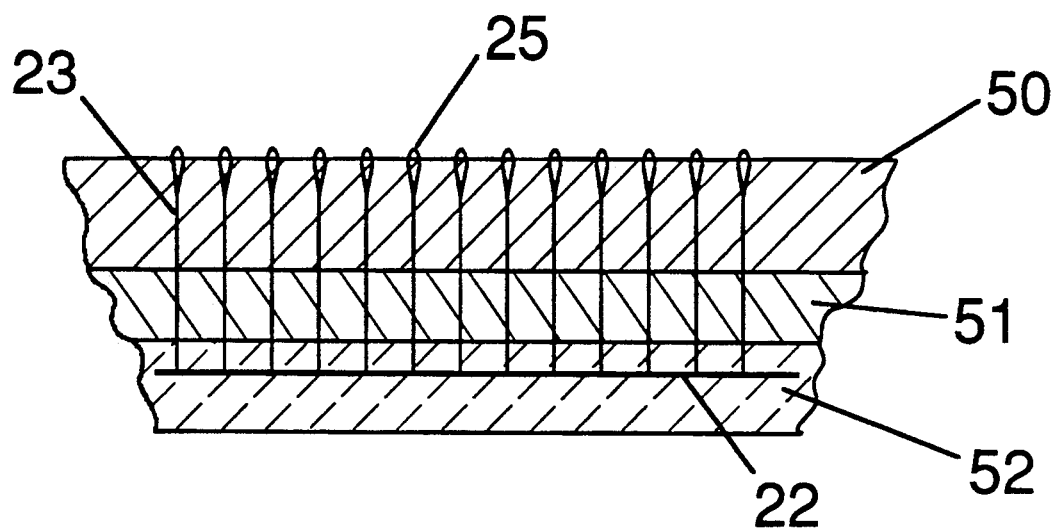
FIG. 2. is a cross-sectional view of the scalp showing the base filament and anchors implanted.
Figure 3:
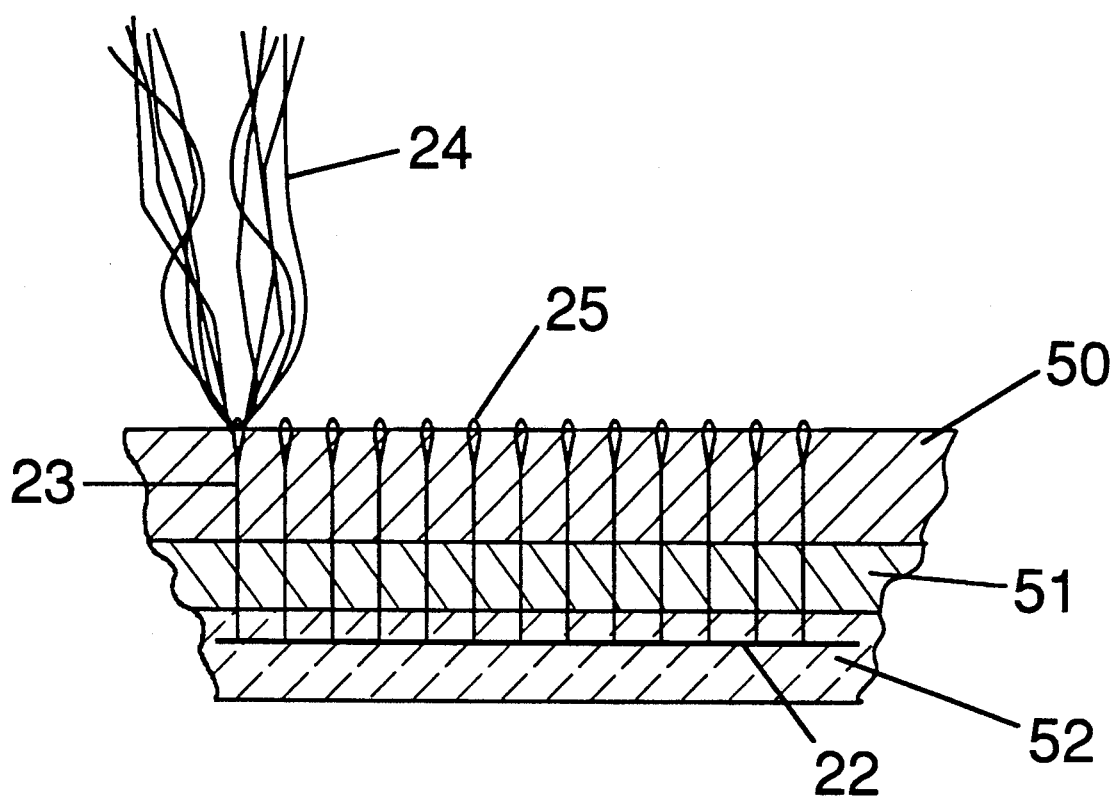
FIG. 3. is a cross-sectional view of the scalp showing hairs attached to the implanted anchors.
Figure 4:
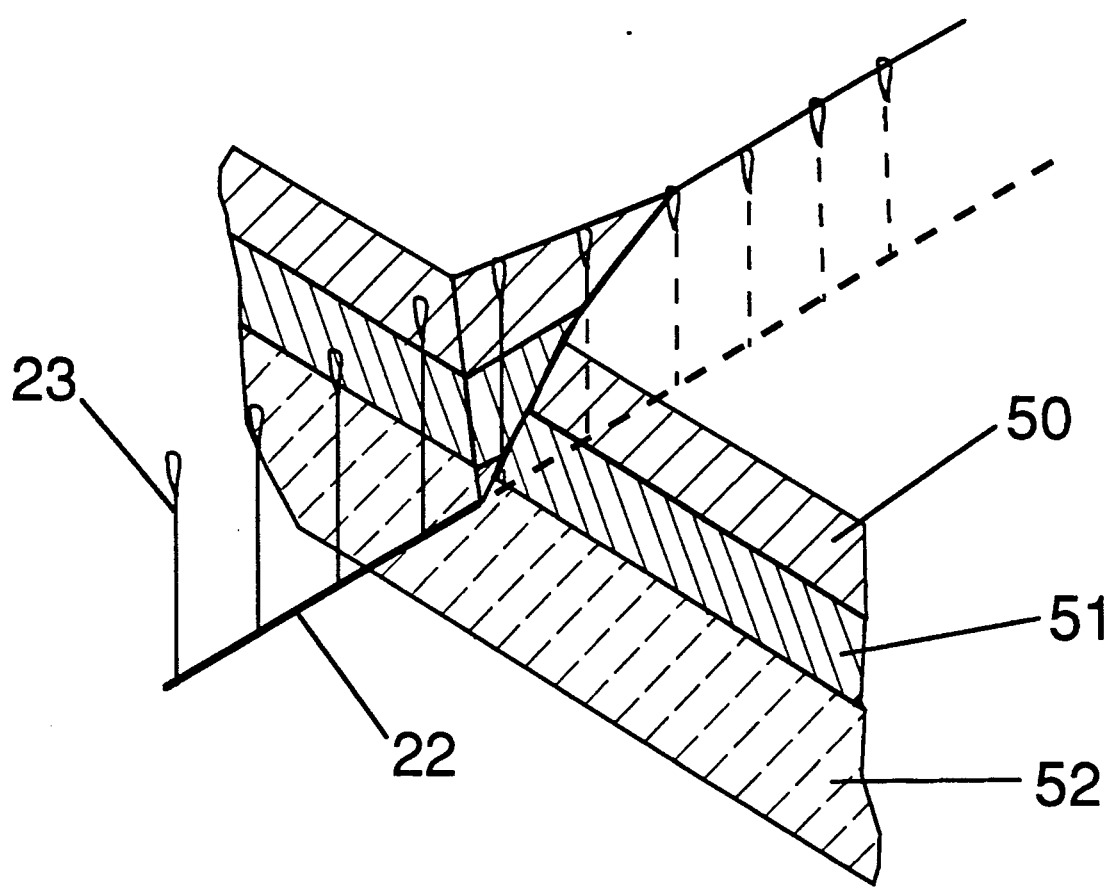
FIG. 4. is a perspective view of the implementation of the base filament and anchors implanted in a person's scalp.
Figure 5:
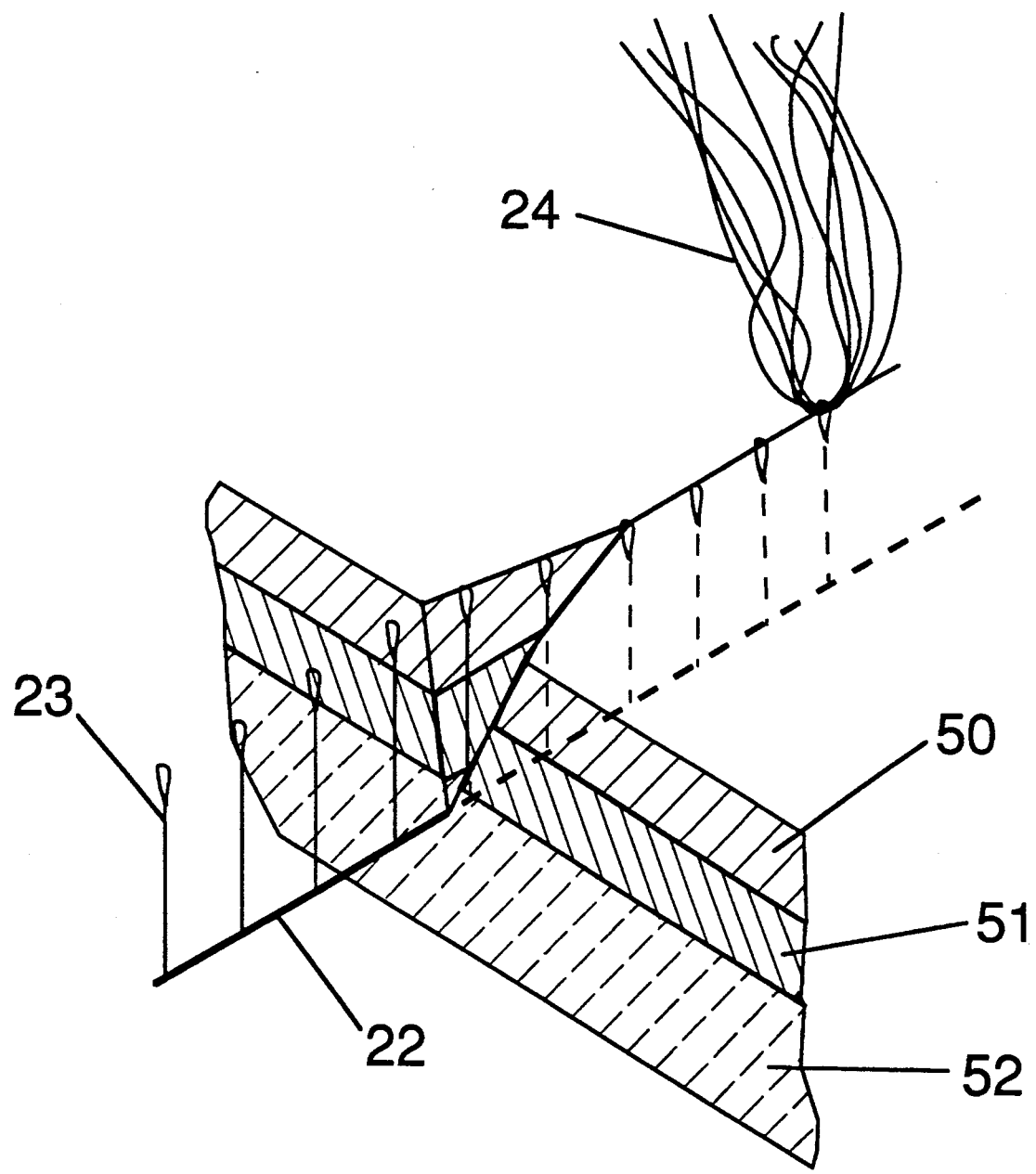
FIG. 5. shows hairs attached to the anchors in a perspective view.
Figure 6:
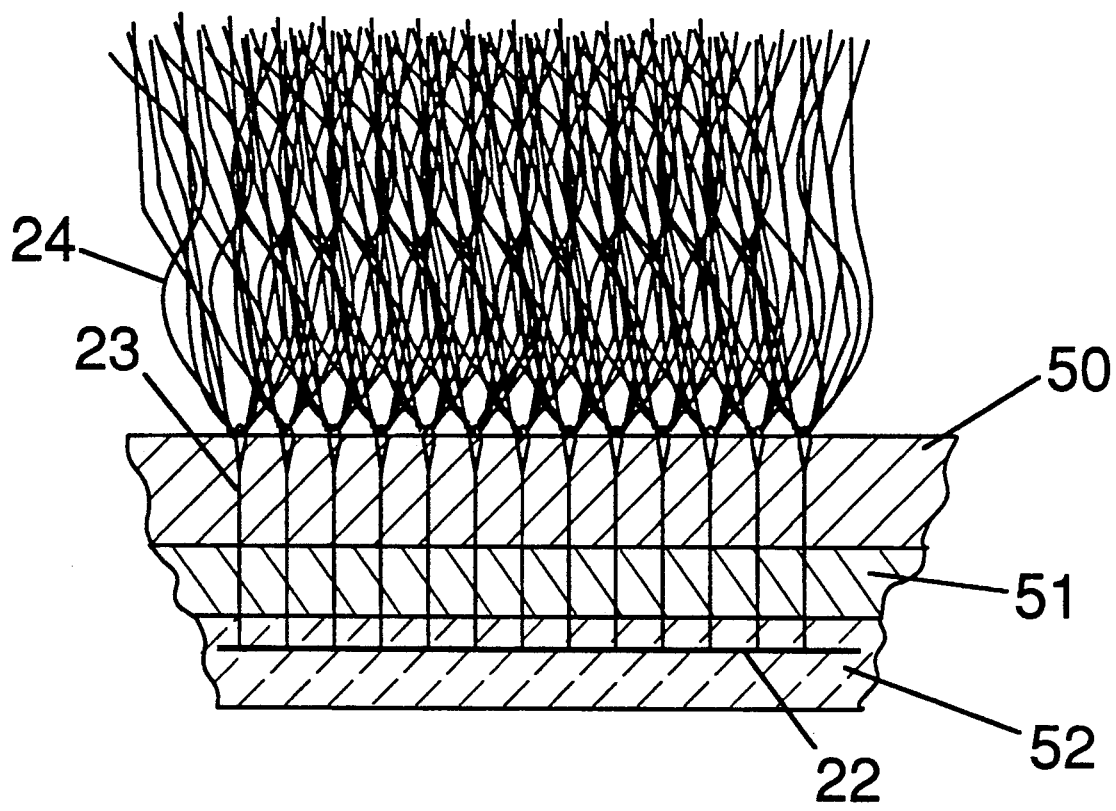
FIG. 6. is a cross-sectional view of the scalp with hairs attached to multiple anchors.
Figure 7:
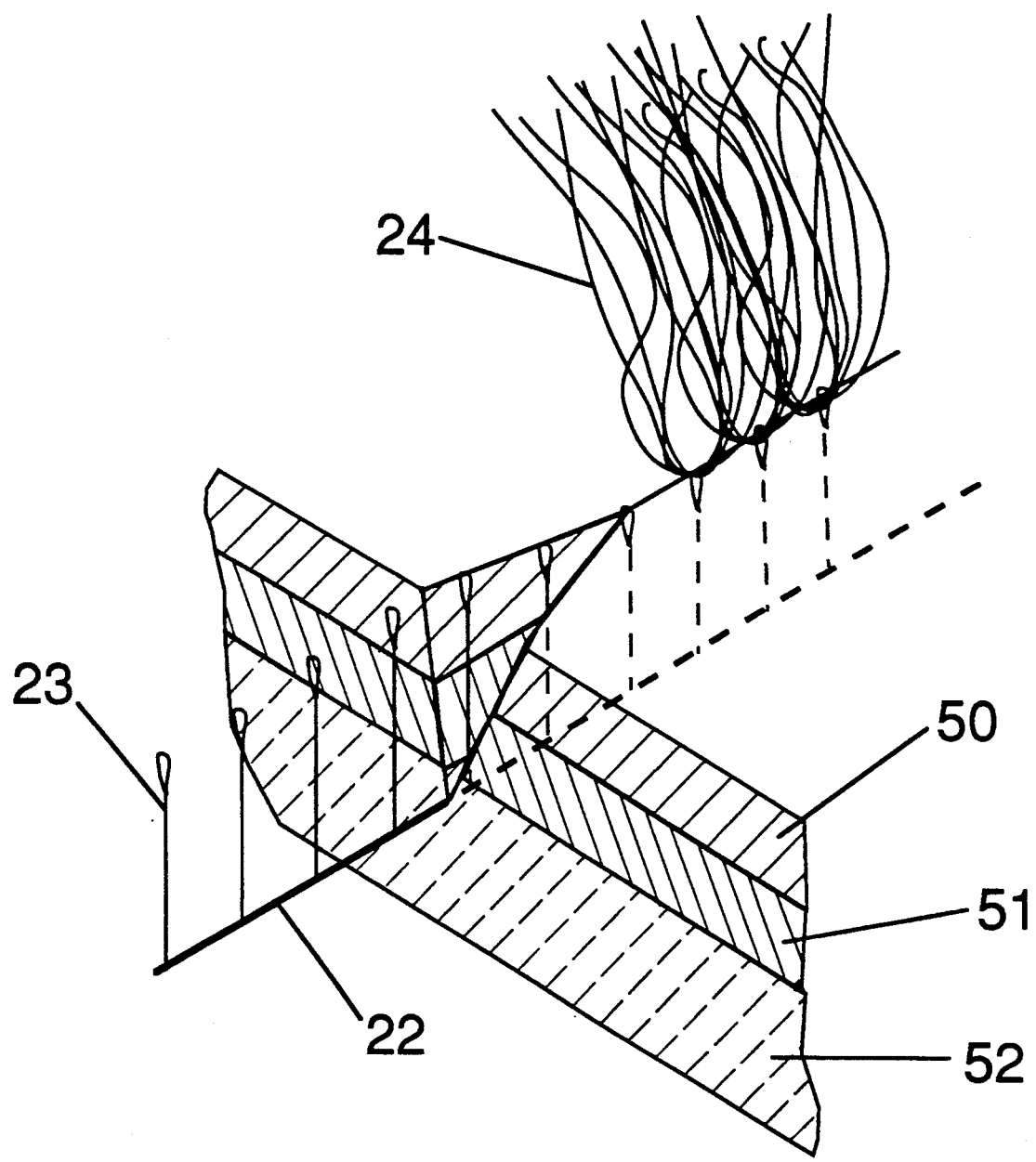
FIG. 7. is a perspective view of the scalp in cross-section with hairs attached to multiple anchors.
Figure 8:
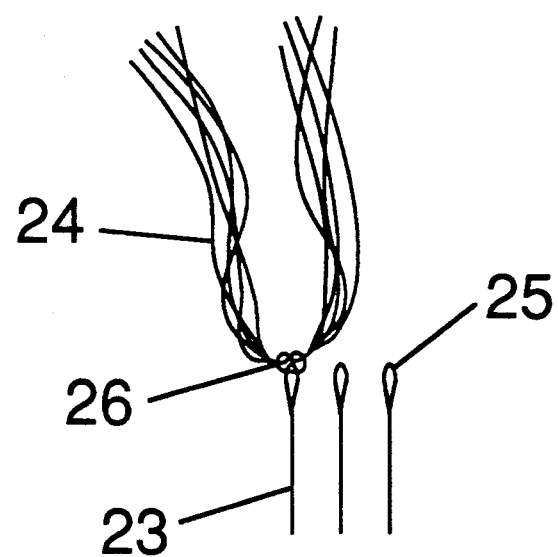
FIG. 8. is drawing showing how the hair may be tied to the anchor.
Figure 9:
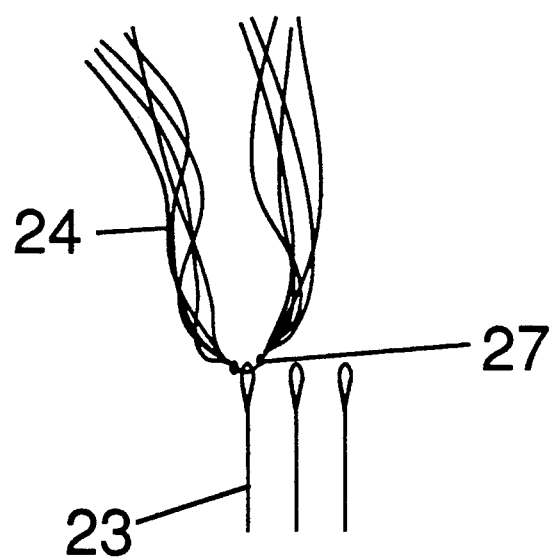
FIG. 9. is a drawing showing the retainers that hold the hair to the anchor.

FIG. 2 and FIG. 4 show the anchors 23 implanted in the scalp. The drawing shows the implant beneath the epidermis 50 and the dermis 51, and in the subcutaneous layer 52. Irrigation of the incision with appropriate antiseptic solutions is obviously necessary during this procedure. After the implant is placed into the incision, the incision may be closed. The incision may be closed through the use of sutures and/or tissue adhesive, if needed. The implant should be placed at a depth such that only the tip of the anchor is exposed at the surface of the scalp. The anchor will terminate with a loop or eyelet which will allow synthetic or natural hair fibers to be attached to it as shown in FIG. 3 and FIG. 5. After hair fibers are attached to multiple, adjacent loops as shown in FIG. 6 and FIG. 7, the density of hair resembles that of normal, growing hair. The hair fibers 24 might be threaded through a loop or eyelet in the anchor 23 as shown in FIG. 8, or held in place with retainers on each side of the anchor as in FIG. 9.

Figure 10:
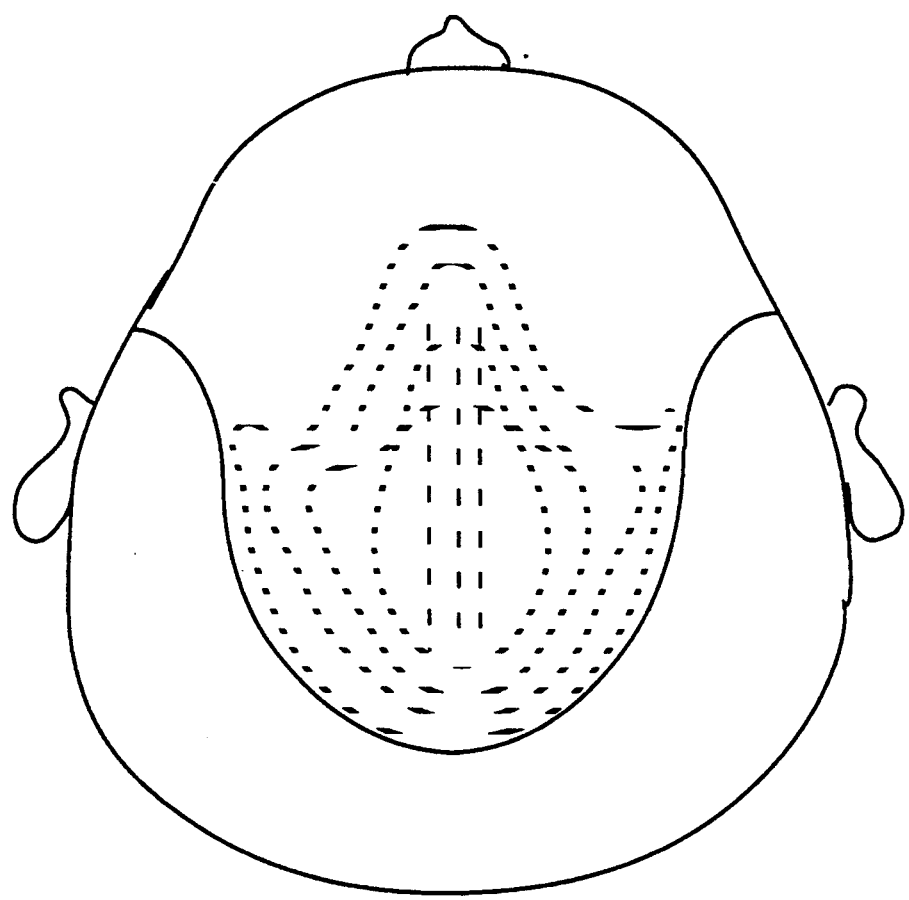
FIG. 10. is a top view of the head showing a typical placement of the implants in the scalp.

Due to the flexible nature of the base filament, the implants could be placed in the scalp in either a curved or straight row pattern, as shown in FIG. 10.

Several advantages are realized by applying the hair 24 after the implant is in place. First, the implantation procedure is simplified because the implant is smaller and easier to handle and position. Second, the implant is not hidden by the hair fibers, hence the scalp can be closely monitored during the healing process. Third, various disinfectants such as hydrogen peroxide may be used without fear of bleaching the hair fibers. Fourth, because the hair is completely above the scalp, a broader range of fibers can be used without concern for their reaction with the subcutaneous tissues 52. Additionally, the number of hair fibers attached to each anchor can be varied. This allows for a variation in density of hair coverage as desired. The most important advantage is due to the fact that the hair can be replaced without disturbing the implants. This would allow for changes in hair style and color. Also, natural degradation of the hair fiber is unavoidable and replacement is inevitable. Most fibers used in hair replacements will not sustain a presentable appearance for more than two years.

I claim:

1. A method of securing hair fibers to a scalp comprising:
   a) implanting in a subcutaneous layer an elongated base filament substantially parallel to the scalp, said base filament having a plurality of anchor filaments extending perpendicularly therefrom, said anchor filaments having a length sufficient to span the epidermis and dermis and terminating in an eyelet such that only a tip of said eyelet is exposed to the dermal surface of the scalp; and
   b) attaching a plurality of hair fibers selected from the group consisting of synthetic and natural fibers to each of said anchors filaments by threading said hair fibers through said eyelets at the dermal surface.

* * * * *